(12) United States Patent
Tomso

(10) Patent No.: US 8,175,813 B2
(45) Date of Patent: May 8, 2012

(54) COMPUTATIONAL METHODS FOR SYNTHETIC GENE DESIGN

(75) Inventor: Daniel J. Tomso, Bahama, NC (US)

(73) Assignee: Athenix Corp., Morrisville, NC (US)

( * ) Notice: Subject to any disclaimer, the term of this patent is extended or adjusted under 35 U.S.C. 154(b) by 598 days.

(21) Appl. No.: 12/248,750

(22) Filed: Oct. 9, 2008

(65) Prior Publication Data

US 2009/0137409 A1    May 28, 2009

Related U.S. Application Data

(60) Provisional application No. 60/978,729, filed on Oct. 9, 2007.

(51) Int. Cl.
*G01N 33/48* (2006.01)
*C12Q 1/68* (2006.01)
*G06F 7/60* (2006.01)
*G06G 7/58* (2006.01)

(52) U.S. Cl. .................. 702/19; 435/6; 702/20; 703/2; 703/11

(58) Field of Classification Search .................. None
See application file for complete search history.

(56) References Cited

U.S. PATENT DOCUMENTS

| | | | |
|---|---|---|---|
| 5,380,831 A | 1/1995 | Adang et al. | |
| 5,500,365 A | 3/1996 | Fischhoff et al. | |
| 5,567,600 A | 10/1996 | Adang et al. | |
| 5,567,862 A | 10/1996 | Adang et al. | |
| 5,625,136 A | 4/1997 | Koziel et al. | |
| 5,763,241 A | 6/1998 | Fischhoff et al. | |
| 5,880,275 A | 3/1999 | Fischhoff et al. | |
| 6,013,523 A | 1/2000 | Adang et al. | |
| 6,015,891 A | 1/2000 | Adang et al. | |
| 6,051,760 A | 4/2000 | Koziel et al. | |
| 6,075,185 A | 6/2000 | Koziel et al. | |
| 6,121,014 A | 9/2000 | Koziel et al. | |
| 6,320,100 B1 | 11/2001 | Koziel et al. | |
| 6,403,865 B1 | 6/2002 | Koziel et al. | |
| 6,720,488 B2 | 4/2004 | Koziel et al. | |
| 6,953,835 B2 | 10/2005 | Fischhoff et al. | |
| 2001/0003849 A1 | 6/2001 | Barton et al. | |
| 2002/0048799 A1 | 4/2002 | Adang | |
| 2003/0046726 A1 | 3/2003 | Koziel et al. | |
| 2003/0192078 A1 | 10/2003 | Fischhoff et al. | |
| 2003/0237117 A1 | 12/2003 | Koziel et al. | |
| 2006/0021095 A1 | 1/2006 | Koziel et al. | |
| 2006/0095988 A1 | 5/2006 | Fischhoff et al. | |

FOREIGN PATENT DOCUMENTS

| | | |
|---|---|---|
| EP | 0 359 472 B1 | 3/1990 |
| EP | 0 385 962 B1 | 9/1990 |
| EP | 0 413 019 B1 | 2/1991 |
| WO | WO 90/10076 A1 | 9/1990 |

OTHER PUBLICATIONS

U.S. Appl. No. 08/434,105, filed May 3, 1995, Fischhoff & Perlak.
Richardson, S.M., et al., "GeneDesign: Rapid, Automated Design of Multikilobase Synthetic Genes," *Genome Research*, Apr. 2006, pp. 550-556, vol. 16, No. 4.
Villalobos, A., et al., "Gene Designer: A Synthetic Biology Tool for Constructing Artificial DNA Segments," *BMC Bioinformatics*, Jun. 6, 2006, vol. 7.
Wu, G., et al., "The Synthetic Gene Designer: A Flexible Web Platform to Explore Sequence Manipulation for Heterologous Expression," *Protein Expression & Purification*, Jun. 1, 2006, pp. 441-445, vol. 47, No. 2.

*Primary Examiner* — Shubo Zhou
(74) *Attorney, Agent, or Firm* — Destiny M. Davenport

(57) ABSTRACT

The present invention is drawn to methods for designing synthetic nucleotide sequences encoding polypeptides of interest. The methods involve organizing a database of sequences as a set of N-length oligomer sequences and compiling a list of probability scores for each N-length sequence. The probability scores are used to substitute one or more higher-scoring sequences into the parent nucleotide sequence to generate an optimized sequence. The nucleotide sequence of interest may be further optimized by removing either or both of unintended open reading frames or undesired short DNA elements, and/or substituting oligomer sequences to achieve a specific G:C content. These methods may be used for optimizing expression of heterologous genes in any organism, particularly in plants. The method generates synthetic sequences with a composition similar to that of a target database. These synthetic sequences may be used, for example, for regulating pesticidal activity or herbicide resistance in organisms, particularly plants or plant cells.

11 Claims, 2 Drawing Sheets

A B C D E F G H I J K (length = 11)
A B C D E
  B C D E F
    C D E F G
      D E F G H         } sequence for each
        E F G H I         NLR where N = 5
          F G H I J
            G H I J K A B C D E: for this NLR, and all NLRs
of length 5, there are $4^5$ possible NLSs
(A,T,G,C at position "A," A,T,G, or C
at position "B," etc.

Of the $4^5$ possible NLSs, a subset will maintain the reading frame
and not disturb the amino acid sequence of the resulting protein;
this subset is determined, and designated as the silent NLSs, or
SNLSs

FIG. 2

SEQUENCE LISTING

<160> NUMBER OF SEQ ID NOS: 60

<210> SEQ ID NO 1
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 1 aatgaa      6

<210> SEQ ID NO 2
<211> LENGTH: 5
<212> TYPE: DNA

```
<213> ORGANISM: Artificial Sequence
<220> FEATURE:
<223> OTHER INFORMATION: oligonucleotide sequence

<400> SEQUENCE: 2 attta                                                                    5

<210> SEQ ID NO 3
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 3 aaaaa                                                                    5

<210> SEQ ID NO 4
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 4 aaaac                                                                    5

<210> SEQ ID NO 5
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 5 aaaag                                                                    5

<210> SEQ ID NO 6
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 6 ttttt                                                                    5

<210> SEQ ID NO 7
<211> LENGTH: 15
<212> TYPE: DNA
<213> ORGANISM: Artificial Sequence
<220> FEATURE:
<223> OTHER INFORMATION: oligonucleotide sequence

<400> SEQUENCE: 7
agtgcaagta cgtaa                                                        15

<210> SEQ ID NO 8
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 8 aataaa                                                                   6
```

```
<210> SEQ ID NO 9
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 9 aatatt                                                                     6

<210> SEQ ID NO 10
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 10 aaccaa                                                                     6

<210> SEQ ID NO 11
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 11 atacta                                                                     6

<210> SEQ ID NO 12
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 12 gataaa                                                                     6

<210> SEQ ID NO 13
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 13 atataa                                                                     6

<210> SEQ ID NO 14
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 14 ataaaa                                                                     6

<210> SEQ ID NO 15
<211> LENGTH: 6
<212> TYPE: DNA
<213> ORGANISM: Artificial Sequence
<220> FEATURE:
<223> OTHER INFORMATION: oligonucleotide sequence
```

```
<400> SEQUENCE: 15 attaat                                                                    6

<210> SEQ ID NO 16
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 16 aataat                                                                    6

<210> SEQ ID NO 17
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 17 aataag                                                                    6

<210> SEQ ID NO 18
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 18 aatcaa                                                                    6

<210> SEQ ID NO 19
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 19 atgaaa                                                                    6

<210> SEQ ID NO 20
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 20 aagcat                                                                    6

<210> SEQ ID NO 21
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 21 atacat                                                                    6

<210> SEQ ID NO 22
<211> LENGTH: 6
<212> TYPE: DNA
```

```
<213> ORGANISM: Artificial Sequence
<220> FEATURE:
<223> OTHER INFORMATION: oligonucleotide sequence

<400> SEQUENCE: 22 aaaata                                                                     6

<210> SEQ ID NO 23
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 23 attaaa                                                                     6

<210> SEQ ID NO 24
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 24 aattaa                                                                     6

<210> SEQ ID NO 25
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 25 aataca                                                                     6

<210> SEQ ID NO 26
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 26 cataaa                                                                     6

<210> SEQ ID NO 27
<211> LENGTH: 6
<212> TYPE: RNA
<213> ORGANISM: Artificial Sequence
<220> FEATURE:
<223> OTHER INFORMATION: sequence capable of forming hairpin loops

<400> SEQUENCE: 27 cuucgg                                                                     6

<210> SEQ ID NO 28
<211> LENGTH: 7
<212> TYPE: RNA
<213> ORGANISM: Artificial Sequence
<220> FEATURE:
<223> OTHER INFORMATION: sequence capable of forming hairpin loops

<400> SEQUENCE: 28 ucuucgg                                                                    7
```

```
<210> SEQ ID NO 29
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 29 tgaga                                                                       5

<210> SEQ ID NO 30
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 30 acttc                                                                       5

<210> SEQ ID NO 31
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 31 tgagg                                                                       5

<210> SEQ ID NO 32
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 32 tgctg                                                                       5

<210> SEQ ID NO 33
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 33 aagctt                                                                      6

<210> SEQ ID NO 34
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 34 gtcttc                                                                      6

<210> SEQ ID NO 35
<211> LENGTH: 5
<212> TYPE: DNA
<213> ORGANISM: Artificial Sequence
<220> FEATURE:
<223> OTHER INFORMATION: oligonucleotide sequence
```

```
<400> SEQUENCE: 35 ggtgt                                                              5

<210> SEQ ID NO 36
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 36 caaag                                                              5

<210> SEQ ID NO 37
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 37 ggatc                                                              5

<210> SEQ ID NO 38
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 38 aagat                                                              5

<210> SEQ ID NO 39
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 39 atttg                                                              5

<210> SEQ ID NO 40
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 40 tgggc                                                              5

<210> SEQ ID NO 41
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 41 ccttc                                                              5

<210> SEQ ID NO 42
<211> LENGTH: 5
<212> TYPE: DNA
```

```
<213> ORGANISM: Artificial Sequence
<220> FEATURE:
<223> OTHER INFORMATION: oligonucleotide sequence

<400> SEQUENCE: 42 accgc                                                                5

<210> SEQ ID NO 43
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 43 ccaac                                                                5

<210> SEQ ID NO 44
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 44 gggac                                                                5

<210> SEQ ID NO 45
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 45 acagg                                                                5

<210> SEQ ID NO 46
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 46 tcgag                                                                5

<210> SEQ ID NO 47
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 47 tcacc                                                                5

<210> SEQ ID NO 48
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 48 acctc                                                                5
```

```
<210> SEQ ID NO 49
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 49 tcaaa                                                                    5

<210> SEQ ID NO 50
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 50 cgtctc                                                                   6

<210> SEQ ID NO 51
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 51 tcagc                                                                    5

<210> SEQ ID NO 52
<211> LENGTH: 6
<212> TYPE: DNA
<213> ORGANISM: Artificial Sequence
<220> FEATURE:
<223> OTHER INFORMATION: oligonucleotide sequence

<400> SEQUENCE: 52 ctgcag                                                                   6

<210> SEQ ID NO 53
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 53 tccag                                                                    5

<210> SEQ ID NO 54
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 54 tcgtg                                                                    5

<210> SEQ ID NO 55
<211> LENGTH: 5
<212> TYPE: DNA
<213> ORGANISM: Artificial Sequence
<220> FEATURE:
<223> OTHER INFORMATION: oligonucleotide sequence
```

-continued

```
<400> SEQUENCE: 55 aatca                                                                        5

<210> SEQ ID NO 56
<211> LENGTH: 5
<212> TYPE: DNA
<213> ORGANISM: Artificial Sequence
<220> FEATURE:
<223> OTHER INFORMATION: oligonucleotide sequence

<400> SEQUENCE: 56 tttat                                                                        5

<210> SEQ ID NO 57
<211> LENGTH: 7
<212> TYPE: PRT
<213> ORGANISM: Bacillus thuringiensis

<400> SEQUENCE: 57

Met Ser Glu Leu Lys Gly Lys
1               5

<210> SEQ ID NO 58
<211> LENGTH: 7
<212> TYPE: PRT
<213> ORGANISM: Bacillus thuringiensis

<400> SEQUENCE: 58

Phe Lys Lys Ser Thr Asn Arg
1               5

<210> SEQ ID NO 59
<211> LENGTH: 7
<212> TYPE: PRT
<213> ORGANISM: Bacillus thuringiensis

<400> SEQUENCE: 59

Thr Cys Cys Leu Leu Lys Ile
1               5

<210> SEQ ID NO 60
<211> LENGTH: 6
<212> TYPE: PRT
<213> ORGANISM: Bacillus thuringiensis

<400> SEQUENCE: 60

Glu Phe Ile Pro Val Glu
1               5
```

COMPUTATIONAL METHODS FOR SYNTHETIC GENE DESIGN

CROSS-REFERENCE TO RELATED APPLICATIONS

This application claims the benefit of U.S. Provisional Application No. 60/978,729, filed Oct. 9, 2007, which is hereby incorporated in its entirety by reference herein.

REFERENCE TO SEQUENCE LISTING SUBMITTED ELECTRONICALLY

The official copy of the sequence listing is submitted electronically via EFS-Web as an ASCII formatted sequence listing with a file named "363085_SequenceListing.txt", created on Oct. 9, 2008, and having a size of 11 kilobytes and is filed concurrently with the specification. The sequence listing contained in this ASCII formatted document is part of the specification and is herein incorporated by reference in its entirety.

FIELD OF THE INVENTION

This invention relates to methods for designing synthetic genes for expression in a heterologous organism, such as a plant. Computer-implemented methods are encompassed, as well as computer systems used to perform the methods of the invention.

BACKGROUND OF THE INVENTION

Expression of foreign genes in heterologous hosts such as plant cells has been difficult, and often detectable expression of the product is not obtained (Fischhoff et al. (1987) *Bio/Technology* 5:807-813; Vaeck et al. (1987) *Nature* 328:33-37). Explanations for poor expression include the fortuitous presence of processing sites, leading to non-functional mRNA transcripts in the transgenic host cells; differing codon usage in plants as compared to the original host; and differences in GC content in the gene sequence and resulting primary RNA transcript. DNA structure is comprised of pairs of bases, along a double helix. It is well known that total DNA from different organisms has different distributions of the four nucleotides, adenine (A), thymidine (T), guanosine (G), and cytidine (C). Within a DNA helix, adenine and thymidine form a 'base pair' by hydrogen bonding (an "AT base pair"). Similarly, guanosine forms base pairs only with cytidine (a "GC base pair"). The ratio of such AT base pairs to GC base pairs is often referred to as 'GC content', and is a percentage of the total base pairs that are comprised of GC base pairs, as opposed to AT base pairs. Similarly, 'AT content' refers to the percentage of base pairs that are comprised of AT base pairs. GC content varies not only between different organisms, but can vary within different regions of the DNA of a genome, and even within the different regions of a gene, such as a plant gene. Plant introns have about 70% AT (30% GC) content, whereas exons have about 50% AT (50% GC) content (Wiebauer et al. (1988) *Mol. Cell Biol.* 8:2042-2051).

Due to the difficulty of expressing insecticidal proteins from *Bacillus thuringiensis* (Bt) in plants, various synthetic genes capable of higher levels of expression in transgenic plants have been designed. Adang et al. (U.S. Pat. Nos. 5,380,831, 6,015,891) describe designing synthetic Bt insecticidal proteins to have enhanced expression in plants by modifying the gene to contain codons preferred by highly expressed plant genes. The codons used are selected with regard to the distribution frequency of codon usage employed in highly expressed plant genes. Adang et al. (U.S. Pat. No. 5,567,600) further describe similar methods where the modification comprises reducing the number of codons having GC in codon positions II and III in a region between plant polyadenylation signals. Alternatively, modifications could result in fewer occurrences of the sequence AATGAA (SEQ ID NO: 1).

Fischhoff et al. (U.S. Pat. No. 5,500,365) disclose modified Bt genes that have plant polyadenylation sequences and ATTTA (SEQ ID NO:2) sequences removed. Koziel et al. (U.S. Pat. No. 6,320,100) disclose synthetic Bt insecticidal proteins selected for optimized expression in a plant, produced using codons that most frequently encode each amino acid in maize, and having 60% GC content.

SUMMARY OF INVENTION

Methods for generating a synthetic nucleotide sequence encoding a polypeptide of interest are provided. These methods produce optimized synthetic gene sequences by calculating the probability of occurrence of contiguous short segments of nucleotides in a DNA sequence database, and then using these probabilities to generate synthetic sequences by replacing low-probability nucleotide sequences in a candidate transgene with high-probability sequences. This is preferably accomplished without altering the amino acid sequence of the encoded protein. Importantly, this statistical method enables generation of a transgene that is optimized for expression in a target organism without the need to possess specific knowledge of processing sites or other expression determinants in the target organism.

These methods comprise (1) developing a database of sequences; (2) selecting a length ("N-length") of contiguous nucleotides as a basis for optimization ("N-length oligonucleotides"); (3) organizing the database of sequences as a set of N-length oligomer sequences; (4) selecting an input sequence; (5) developing a set of silent NLSs ("SNLS") for the input sequence; and, (6) optimizing among the choices of SNLS to yield an optimized gene sequence.

These methods may, alternatively or in addition, comprise removing unwanted open reading frames, and/or modifying the nucleotide sequence of interest to remove unwanted short consensus nucleotide sequences, and/or achieve a desired GC content for the resulting optimized gene, without consideration of codon usage.

The methods of the invention are useful for the production of nucleotide sequences optimal for expression in an organism, particularly plants and bacteria, to provide pesticidal or herbicide resistance activity. Such organisms are desirable for agricultural purposes. The methods of the invention are also useful for generating altered or improved proteins that have pesticidal or herbicide resistance activity, or for detecting the presence of pesticidal or herbicide resistant proteins or nucleic acids in products or organisms.

DESCRIPTION OF FIGURES

FIG. 2 show a diagrammatic example of determination of NLSs

DETAILED DESCRIPTION

Figure 1:
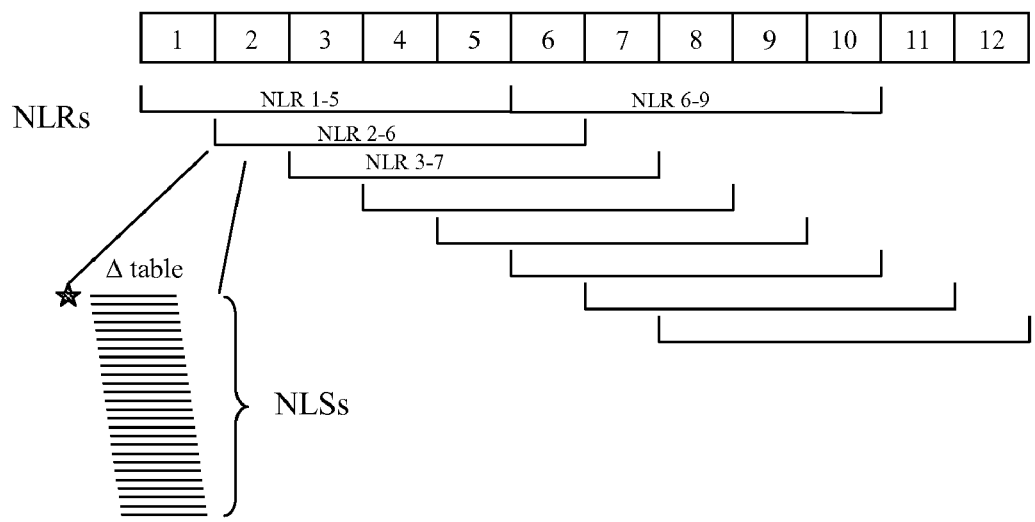
FIG. 1 shows an illustration of the relationship between NLRs, NLS, and delta table. In this illustration A, B, C, D, and E represent hypothetical positions within a nucleotide region (NLR) of length five (N=5). The figure illustrates a subset of the NLSs that may be generated for this NLR. Thus, for all NLRs of length 5 there are $4^5$ possible NLSs (A, T, G, or C at position A; A, T, G, or C at position B; etc.).

Previous methods for synthetic gene design fall generally into two categories. The first uses specific knowledge of processing signals, such as polyadenylation signals, to design transgenes with a higher probability of expression in a target organism (e.g. Fischhoff et al). This strategy is applicable only in situations where specific experimental knowledge of such processing signals is available. Additionally, incomplete knowledge of processing determinants in expressed genes could result in improper modification of a transgene, resulting in little or no expression in the target organism. The second category of methods depends entirely on codon bias and/or GC content correction to improve expression of transgenes (e.g. Koziel et al, Adang et al), in spite of ample evidence for the significant role of higher-order DNA sequence determinants (e.g. ATTTA, AATGAA).

The present invention is drawn to methods for designing synthetic nucleotide sequences encoding polypeptides of interest. The methods involve (1) organizing a database of sequences as a set of N-length oligomer sequences ("NLSs"); (2) generating an NLS Stats Table by determining and compiling the observed probability for each NLS among the population of all possible NLSs; (3) developing a set of NLRs for the sequence of interest; (4) determining the set of NLSs that do not disrupt the open reading frame ("silent NLSs", or "SNLS"); and, (5) optimizing the choices among SNLS assemblies to yield an optimized nucleotide sequence.

In another aspect of the invention, the nucleotide sequence of interest is analyzed and adjusted to remove either or both of (1) unintended open reading frames or (2) undesired short DNA elements. An "unintended ORF" is an ORF that is different from the ORF of the parent sequence and arises through modification of the sequence using the methods of the invention. "Undesired short DNA elements" include stretches of DNA that introduce structures not optimal for expression in a target organism. Exemplary short DNA elements are discussed elsewhere herein.

These methods may be used for optimizing expression of heterologous genes in any organism, particularly in plants. The method generates synthetic sequences with a composition similar to that of a target database. These synthetic sequences may be used, for example, for regulating pesticidal activity or herbicide resistance in organisms, particularly plants or plant cells.

Definitions

In order to understand the invention clearly it is useful to have the following definitions:

By "synthetic" is intended that which does not occur in nature. For the purposes of the present invention, a synthetic sequence is not intended to encompass sequences arising from naturally-occurring mutations, or from mutations that are induced by chemical or biological mechanisms, such as site-directed mutagenesis, and the like. In some embodiments, a synthetic nucleotide sequence is or is intended to be chemically synthesized in its entirety or for the greater part of the coding region. Methods to chemically synthesize nucleotide sequences are well known in the art (see, for example, Ausubel et al., eds. *Current Protocols in Molecular Biology* (2000) Chapter 8.2B, Vol. 1, John Wiley & Sons, New York; Xiong et al. (2004) *Nucleic Acids Res.* 32:e98; Ovchinnikov et al. (1984) *Gene* 31:65-78; Khudyakov et al. (1993) *Nucleic Acids Res.* 21:2747-2754).

A synthetic sequence includes a nucleotide sequence that varies from a naturally-occurring parent sequence in at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the nucleotide positions corresponding to the parent. It will be appreciated that nucleotide sequences can be optimized within certain regions of the sequence, where the remainder of the sequence remains unchanged relative to the parent sequence. For the purposes of the present invention, the terms "synthetic nucleotide sequence" and "optimized nucleotide sequence" are used interchangeably.

By "N-length region," or "NLR," is intended a contiguous nucleotide sequence of length N that corresponds to a region of the nucleotide sequence of interest. For example, an NLR can be from about 1 to about 100 nucleotides in length, or from about 2 to about 50, or from about 3 to about 40, or from about 4 to about 30, or from about 5 to about 20, or from about 6 to about 15, or about 10 nucleotides in length. In some embodiments, the NLR is greater than or less than 3 nucleotides in length.

By "N-length sequence" or "NLS" is intended any contiguous nucleotide sequence of length N. For any given optimization run, the length of each NLS is equal to the length of each NLR. See, for example, FIG. 1. In this example, the nucleotide sequence of interest is represented by 12 nucleotides, and each NLR is 5 nucleotides in length. Thus, each NLS for each NLR is also 5 nucleotides in length.

It is understood that the methods described herein can be employed to generate a single optimized sequence from a single nucleotide sequence of interest, as well as multiple different optimized sequences from a single nucleotide sequence of interest. Where multiple different optimized sequences are generated, one or more of the optimization parameters is changed in each optimization run such that a different optimized sequence is generated from that run. One such parameter that can be varied is the value represented by "N" in the NLS and the NLR.

The steps of the method disclosed herein are set forth in the following modules.

Module A. Develop a Target Database

The method of the invention requires a target database of nucleotide sequences. The "target database" can be any database of one or more nucleotide sequences, for example the GENBANK® nucleotide database, a database of sequences specific to a certain genus or species (e.g., a maize-specific database, a soybean-specific database, an animal-specific database such as a human, laboratory, or agricultural animal-specific database, etc.), or a custom database of nucleotide sequences that would be relevant for the particular user. In one embodiment, the target database comprises a collection of coding sequences for an organism of interest. The database of sequences may be organized in any number of formats or file types, for example as a file of files in FASTA format, or as a folder of sequence files in a computer readable format.

Module B. Organize Database as Set of N-Length Oligomer Sequences

In this aspect of the invention, one organizes the data from the target database in the form of an NLS Statistics Table (or an "NLS Stats Table"). The NLS Stats Table is generated by setting the length "N" and determining the frequency of every possible N-length segment represented in that database. The value of N can be arbitrarily selected based on the size of the target database (i.e., across all sequences in that database). Generally, longer NLR sequences capture more information than shorter NLR sequences, but the number of NLS Stats Table entries is governed by sequence length, and overlylarge tables slow algorithm execution and decrease statistical precision. An empty NLS Stats Table is generated by first listing every possible sequence of length n. For example, for n=5, the NLS Stats Table would have 1024 entries (AAAAA, AAAAC, AAAAG . . . TTTT (SEQ ID NO:3-6, respectively).

An NLS Stats Table can be compiled by counting the number of times each NLS is represented in the database, for example through the use of a "sliding window" algorithm that scans every sequence in the database. Alternatively, an NLS Stats Table could be compiled by using any other statistically reasonable strategy, for example by random sampling of short sequences from a database. Sliding window algorithms are known in the art. In one embodiment, the algorithm moves along each sequence in the target database by sliding one or more nucleotide(s) at a time to compile the list of NLSs. For example, in a hypothetical target database comprising a nucleotide sequence represented by AGTGCAAGTACG-TAA (SEQ ID NO:7), where N is set to 5, the first NLS is AGTGC, the second NLS is GTGCA, the third NLS is TGCAA, and so forth. A set of NLSs is compiled for every sequence in the target database. The sliding window algorithm counts the number of times each NLS from the empty NLS stats table is represented in the database. For example, the algorithm scans all sequences and counts the number of times the NLS "AAAAA" appears in the database, the number of times the NLS "AAAAC" appears in the database, the number of times the NLS "AAAAG" appears, etc. This raw count is then divided by the total number of NLSs observed in the database to give an observed frequency value.

For each NLS, a probability score is calculated, which represents the observed frequency of each NLS relative to its expected frequency of occurrence within the target database. In one example, the probability score is converted to a log probability score and is equal to the $\log_{10}$[observed frequency of the NLS in the database/expected frequency of the NLS in the database].

The method of calculation of the expected frequencies can vary. In one aspect, each nucleotide is considered equally probable. In this case the expected frequency would be $0.25^N$, where N is the length designated for the NLR/NLS above. Thus, for the example 5-mer NLS discussed supra (AGTGC), the expected frequency would be $0.25^5 = 0.0098$.

In other embodiments, a frequency that is based on the relative frequency of each nucleotide in the target database is used. The relative frequency of each nucleotide is calculated as the fractional representation of nucleotides G, C, T, and A across the entirety of all of the sequences (collectively) in the target database (the 'database frequency' for that nucleotide). In this case, the expected frequency for the NLS is calculated for each N-length sequence by, (1) for each position in the NLS, recording the database frequency of the nucleotide represented at that position (A, G, C, or T); and then (2) calculating the product of those database frequencies to generate an expected frequency for the entire NLS. For example, if the base composition of the entire database is A=0.20, G=0.30, T=0.20 and C=0.30, the expected frequency of the NLS "AGTGC" would be 0.2×0.3×0.2×0.3×0.2=0.00072.

In cases where the observed frequency of a particular NLS in the database is greater than the calculated expected frequency, the ratio of observed/expected is greater than one and the log probability score is a positive number. In cases where the observed frequency is lower than the expected frequency, the ratio is less than one and the log probability score is a negative number. Thus, for each NLS, a positive log probability means that the NLS is observed more often than would be expected statistically, and a negative log probability means the NLS is observed less often than would be expected statistically.

In cases where a given NLS is not observed in the database (i.e. where the observed frequency is zero), an approximation is used. In one example, the observed frequency is set to [1/1+the total number of NLSs observed in the database]. In another example, an arbitrary value lower than the lowest observed frequency in the NLS Stats table is selected. Consequently, unobserved NLSs typically have very low probability scores relative to observed NLSs.

Scoring Module

In one aspect of the invention, Module B can be used to assess the fit of a particular sequence (or sequences) to an NLS Stats Table. For example, the sequence of interest can be scanned to look for low scoring regions, or an aggregate score for the entire sequence can be calculated. This aggregate score can be used, for example, to compare two different nucleotide sequences encoding the same amino acid to determine which sequence would be a better fit for expression in a target organism. While not bound by any particular theory or mechanism, it is proposed that sequences having a preponderance of low scoring regions (or sequences having a lower aggregate score) will have lower levels of expression in the target organism than sequences having a preponderance of higher scoring regions (or sequences with a higher aggregate score). One method to evaluate the fit of a sequence to an NLS Stats table comprises:

a. Providing an NLS Stats table (e.g., an NLS Stats table for a target organism in which the sequence of interest is to be expressed);
  b. Identifying every NLR within the sequence of interest, for example by using a sliding window algorithm as described above;
  c. For each NLR, reading the NLS at that position;
  d. Using an NLS Stats table, looking up the log probability score of each NLS identified in steps b and c. This NLS probability value is used as a probability value for each NLR position in the sequence of interest.
  e. Summing the log probability scores for all NLR positions to develop a total score for the sequence of interest. Note that summing logs scores is equivalent to multiplying base (non-log) probability values.
  f. This method provides an aggregate score for the entire sequence.

Another method for evaluating the fit of a sequence to an NLS Stats Table involves looking for low-scoring segments within a larger sequence of interest. Such low-scoring segments may represent significant barriers to transgene expression, or may be sufficient to disrupt expression. This method comprises:

a. Subdividing a sequence of interest into smaller segments. Such segments can be overlapping. For example, a 1000-bp sequence could be divided into 50-bp segments.
  b. Scoring each segment thus identified using a method similar to that described above.
  c. Recording the scores for each segment.
  d. Assigning a score to the entire sequence that is equivalent to the lowest-scoring segment in the sequence.

Module C. Optimization Module

When the nucleotide sequence of interest is a coding sequence for a protein of interest, it will be necessary to evaluate the list of all possible NLSs at each given NLR and identify those NLSs that do not disrupt the open reading frame and/or the encoded amino acid sequence (i.e. are 'silent' with respect to the protein translation). The sets of such NLSs are herein referred to as lists of silent NLSs or "SNLS."

In one aspect of the invention, the SNLS lists are developed by using the entire sequence of interest as a basis for translation and evaluation. This method comprises:
  a. For each NLR within a sequence of interest, substituting every possible NLS into the original sequence of interest at that position. For example, for n=5, there are 1024 possible sequences (AAAAA, AAAAC, AAAAG . . . TTTTT).
  b. Translating both the entire original sequence of interest and newly-generated substituted sequence into amino acid sequences.
  c. Comparing the two amino acid sequences. If the two translations are identical, the substitution is considered silent and the NLS used in that round is added to the SNLS list for that NLR position.
  d. After evaluating every possible NLS, the list of SNLSs for that position is complete.

In another aspect of this invention, the SNLS list is developed by performing only limited translation and comparison in the immediate vicinity of the NLR being examined. This method is computationally preferred versus the method described above. This method comprises:
  a. For each NLR within a sequence of interest, establishing a translatable in-frame window around the NLR. This is accomplished by expanding the NLR in the 5' and/or 3' directions such that, i) the length of the region becomes a multiple of 3 (to accommodate the triplet nature of the genetic code), and ii) the starting position of the expanded region is in-frame with translation frame of the original full-length (i.e., parent) sequence.
  b. Using the parent sequence that corresponds to this expanded region as a base sequence, substituting every possible NLS into the base sequence at a position that corresponds to the starting NLR in step a.
  c. Translating both the original base sequence and the newly-generated substituted sequence into amino acid sequences.
  d. Comparing the two amino acid sequences. If the two translations are identical, the substitution is considered silent and the NLS used in that round is added to the SNLS list for that NLR position.
  e. After evaluating every possible NLS, the list of SNLSs for that position is complete.

In another aspect of this invention, the SNLS list is generated by first creating a translated peptide for each NLR, and then selecting SNLS members from the set of all degenerate nucleotide sequences that could encode the translated peptide. This method comprises:
  a. For each NLR within a sequence of interest, establishing a translatable in-frame window around the NLR. This is accomplished by expanding the NLR in the 5' and/or 3' directions such that, i) the length of the region becomes a multiple of 3 (to accommodate the triplet nature of the genetic code), and ii) the starting position of the expanded region is in-frame with translation frame of the original full-length sequence.
  b. Using the parent sequence that corresponds to this expanded region as a base sequence, generate a target amino acid sequence (i.e. translate the original nucleotide sequence of that region).
  c. Generate the set of all nucleotide sequences that encode the target amino acid sequence. This set of sequences is considered 'degenerate' because of the redundancy of the genetic code.
  d. From the set of degenerate sequences, identify and record the N-length sequence that is in the position that corresponds to the original NLR in step a.
  e. The list of all NLSs identified in step d, minus any duplicates, is the SNLS list for that position.

Next the score of each SNLS is assigned using the NLS Stats Table, and a delta score is calculated for each SNLS. The "delta score" or "Δ" represents the difference of the probability score between the original sequence of the NRL of the nucleotide sequence of interest and each corresponding SNLS (Δ=silent−original). Consequently, a positive delta score indicates that the SNLS is more similar to the sequences in the target database (has a higher probability score) than the original sequence, and the magnitude of the delta score corresponds to the degree of bias observed in the target database. Then, for every NLR, the list of SNLSs is sorted by delta score from highest to lowest. The list of SNLSs that is generated for an individual NLR is referred to herein as the "corresponding SNLS list" for that particular NLR. Thus, each NLR will have its own corresponding SNLS list.

To optimize a sequence, the general strategy is to replace the original NLS at each NLR with a SNLS having the largest delta score. The net effect of these substitutions is to drive the overall composition of the original sequence closer to the composition of the sequences in the target database. At the same time, low-scoring subsegments of the original sequence are replaced with higher-scoring segments while preserving the original translation of the entire sequence.

An exemplary algorithm to perform the steps of this module may include the following steps:
  1) For the sequence to manipulate, set the sequence as "input sequence."
  2) Develop a list of all NLR positions in the input sequence based on the N-length utilized for the NLS stats table. Typically there are [L−N+1] NLR positions in a sequence, where L is the length of the original sequence.
  3) For each NLR, develop a list of corresponding SNLSs.
  4) Choose the top scoring SNLS (e.g., SNLS with the highest delta score) for the entire sequence by examining each corresponding SNLSs list. In the case of the delta scores, the 5'-most position is used first.
  5) For the NLR having the highest scoring SNLS, set the sequence of that NLR to be the sequence of the corresponding highest scoring SNLS.
  6) Temporarily "lock" any NLRs that overlap with the position that was just changed, including the NLR that was changed itself. This step is required to prevent 'flip-flopping' or other cyclical processes where a single limited area is changed back and forth by overlapping substitutions. Locked NLRs are not considered for NLS substitutions during the remainder of this cycle of optimization. However, they are unlocked in subsequent cycles to allow total optimization of the sequence.
  7) Choose the top scoring SNLS for the entire sequence from the list of remaining unlocked NLRs and corresponding SNLS lists.
  8) Repeat steps 5 through 7 until every NLR in the sequence either 1) is locked, or 2) already contains the highest-scoring SNLS for that position. At this point, a single cycle of optimzation has been completed.
  9) Unlock the entire sequence.
  10) Generate a score for the entire sequence using the NLS Stats Table as described above.
  11) Repeat the optimization procedure starting at step 1, using the sequence from the previous cycle as the input sequence.

12) Continue to repeat steps 1 through 11 (i.e. perform sequential optimization cycles) until two consecutive cycles produce identical-scoring sequences. This indicates that no further optimization is possible.

13) Output the sequence from the last cycle as the 'fully-optimized sequence.'

In another aspect of this invention, a preliminary round of optimization is performed directly from the amino acid sequence of the translated parent sequence. This method comprises:

a. Translating the entire parent sequence into an amino acid sequence.

b. Dividing the entire translated gene into contiguous peptide segments. The length of each peptide segment can range from 1 amino acid to the entire length of the translated gene (with each segment being the same length). Lengths of about 3 to about 10 amino acids are preferred with current computer systems.

c. For each peptide segment, creating a set of all nucleotide sequences that encode that segment (a set of degenerate sequences).

d. Scoring each degenerate nucleotide sequence thus generated using an NLS Stats Table generated for the target database (see Module B). This score is calculated by the methods disclosed in the "scoring module" described supra for scoring subsegments of a sequence.

e. Selecting the highest-scoring nucleotide sequence for each peptide segment, and assembling these sequences in order.

f. Passing the preliminary assembled sequence through additional optimization as described above.

In subsequent optional processes (Modules D and E), the optimized sequence from Module C is further analyzed and adjusted to remove any unintended open reading frames or undesirable short DNA sequences.

Module D. Removal of Undesirable Short DNA Sequences

In one aspect of the invention, certain short DNA sequences representing or believed to be capable of representing undesirable features are removed from the optimized sequence. Such short DNA sequences can include certain restriction enzyme recognition sequences, polyadenylation sequences, 5' and or 3' splice recognition sites, and the like. These elements may be defined by the particular user.

In one aspect of the invention, such short DNA sequences are removed from the nucleotide sequence by scanning the sequence for undesired elements and replacing NLSs from NLRs overlapping these short sequences with different NLSs, thereby disrupting the short nucleotide sequence. Preferably, the NLS having the lowest impact on the total score is substituted for an NLS overlapping the undesired element. Methods for calculating total score are discussed elsewhere herein. In the case of optimization of coding DNA sequence, only SNLS substitutions are allowed, and substitutions that introduce spurious (i.e., unintended) ORFs are disallowed. This cycle is typically repeated until no undesirable sites remain, although it may not be necessary to remove every undesirable sequence. Removal of short DNA sequences is typically performed during or after optimization according to Modules A, B and C herein, or can be performed in the absence of either of these modules.

In one aspect of this invention, specific undesirable sequences, such as polyadenylation sites, can be removed from an optimized sequence. In this way, this method can accomplish both general optimization and specific site correction in cases where such knowledge is available. Examples of polyadenylation sites include, but are not limited to, AATAAA, AATATT, AACCAA, ATACTA, AATGAA, GATAAA, ATATAA, ATAAAA, ATTAAT, AATAAT, AATAAG, AATCAA, ATGAAA, AAGCAT, ATACAT, AAAATA, ATTAAA, AATTAA, AATACA, and CATAAA (SEQ ID NO:8-11, 1, and 12-26, respectively) (see, for example, Zhao et al. (1999) *Microbiol. Mol. Biol. Rev.* 63:405-445). Plant-specific polyadenylation sites are described in Joshi (1987) *Nucleic Acids Res.* 15:9627-9640 and Rothnie (1996) *Plant Mol Biol.* 32:43-61. Prokaryotic polyadenylation sites are discussed in Sarkar (1997) *Annu. Rev. Biochem.* 66:173-197. Polymerase termination signals include, but are not limited to, $(CAN)_{7-9}$AGTNNAA (see, for example, Vankan and Filipowicz (1988) *EMBO J.* 7:791-799). Consensus splice sites include, but are not limited to, 5'-AAG:GTAAGT and 3'-TTTT(Pu)TTT(Pu)T(Pu)T(Pu)T (Pu)TGCAG:C (see, for example, Brown et al. (1986) *EMBO J.* 5:2749-2758; Hanley and Schuler (1988) *Nucleic Acids Res.* 16:7159-7176). The most invariant residues of splice sites are the 5'-GT and 3'-AG.

The optimized nucleotide sequence may also be further modified by substitution with NLSs having a lower probability of generating a stable RNA secondary structure. Such secondary structures include, but are not limited to, hairpin loops (snapback structures). Sequences capable of forming hairpin loops include, but are not limited to, CUUCGG (SEQ ID NO:27) and UCUUCGG (SEQ ID NO:28) (see, for example, Tuerk et al. (1988) *Proc. Natl. Acad. Sci. U.S.A.* 85:1364-1368).

In addition, the optimized sequence may be further optimized by eliminating the occurrence of unwanted short nucleotide consensus sequences, such as recognition sites for restriction endonucleases, polyadenylation sequences, 5' and 3' splice recognition sequences, and the like.

Module E. Removal of Additional ORFs

In another aspect of the invention, open reading frames (ORFs) that do not encode the protein of interest are removed from the optimized sequence. This removal of undesired or "spurious" ORFs is accomplished by replacing NLSs at NLR positions internal to the spurious ORF with NLSs that disrupt the spurious ORF. An "internal NLR" is an NLR that falls within the boundaries of the spurious ORF as identified by all-frame translations of the sequence of interest. In this embodiment, the sequence is scanned for the presence or spurious ORFs. Next, NLR positions that are internal to the spurious ORFs are identified. SNLS substitutions at these NLR positions are evaluated, and those that disrupt the spurious ORF are selected based on delta scores as described above. Typically, the SNLS having the lowest impact on the total score is selected. Because only SNLSs are considered, substitutions are selected that disrupt any spurious ORF while not interrupting the primary ORF. This cycle may be iterated to generate increasingly polished optimized sequences, or until spurious ORFs having a length of greater than about 1000, about 900, about 800, about 700, about 600, about 500, about 400, about 300, about 200, about 100, or greater than about 75 nucleotides are removed.

Module F. Optimization of GC Content.

In yet another aspect of the invention, the optimized nucleotide sequences can be further altered to adjust the GC content of the optimized sequence. This alteration can be accomplished by substituting NLSs at NLRs with NLSs having different GC contents. Substitutions that introduce spurious ORFs or undesirable short DNA sequences should be disallowed. In one example, all possible SNLSs at all NLRs are examined, and those having the least impact on the total score while altering net GC content are identified. Substitutions are made iteratively with locking as described above until the total GC content of the gene reaches a target threshold; for example a GC content of about 40 to about 60%, for example about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39% or about 38%.

In one embodiment, the GC content of the optimized nucleotide sequence is uniform across the entire nucleotide sequence. By "uniform across" the nucleotide sequence is intended that the GC content of any defined subsegment of the full-length optimized sequence has a GC content that is similar to the GC content of any other defined subsegment of the full-length optimized sequence. By "similar to" the GC content, it is intended that the GC content of a reference subsegment is within about 20%, within about 19%, within about 15%, within about 10%, within about 9%, within about 8%, within about 7%, within about 6%, within about 5%, within about 4%, within about 3%, within about 2%, within about 1%, or less of the GC content of the subsection to which the reference section is being compared.

Computer-Implemented Methods

The methods described above for generating a synthetic nucleotide sequence may be performed, wholly or in part, with the use of a computer program or computer-implemented method.

Computer programs and computer program products of the present invention comprise a computer usable medium having control logic stored therein for causing a computer to generate a synthetic nucleotide sequence encoding a polypeptide of interest. In one embodiment, the computer program comprises a computer usable medium having control logic stored therein for causing a computer to generate an NLS Stats Table, the control logic comprising a first code for causing the computer to accept external information entered by an input device, wherein the external information comprises a database of DNA sequences and a designation of the n-length. Control logic is also referred to as computer-readable and/or computer-executable code.

In another embodiment, the computer program comprises a computer usable medium having control logic stored therein for causing a computer to generate an optimized nucleotide sequence encoding a polypeptide of interest, the control logic comprising a first code for causing the computer to accept external information entered by an input device, wherein the external information comprises an NLS Stats Table, and a nucleotide sequence to be optimized. Control logic is also referred to as computer-readable and/or computer-executable code.

In another embodiment, the computer program comprises a computer usable medium having control logic stored therein for causing a computer to generate an optimized nucleotide sequence encoding a polypeptide of interest, the control logic comprising a first code for causing the computer to accept external information entered by an input device, wherein the external information comprises the DNA sequence of an optimized nucleotide sequence, and a set of DNA and protein sequences that are less desired (e.g., short undesirable DNA sequences as disclosed elsewhere herein). Control logic is also referred to as computer-readable and/or computer-executable code.

In another embodiment, the computer program comprises a computer usable medium having control logic stored therein for causing a computer to generate a synthetic ("optimized") nucleotide sequence encoding a polypeptide of interest, the control logic comprising a first code for causing the computer to accept external information entered by an input device, wherein the external information comprises a database of DNA sequences, a designation of the n-length, and an amino acid sequence for which to develop optimized gene(s); a second code for causing the computer to generate an NLS Stats Table from the input; a third code for developing a set of NLRs, a fourth code for determining the set of NLSs that do not disrupt the open reading frame ("silent NLSs", or "SNLS"), and a fifth code for optimizing the choices among SNLS assemblies to yield an optimized gene sequence.

Computer systems of the present invention used to generate a synthetic nucleotide sequence encoding a polypeptide of interest comprise a processor, operative to determine, accept, check, and display data, a memory for storing data coupled to said processor, a display device coupled to said processor for displaying data, an input device coupled to said processor for entering external data; and a computer-readable script with at least two modes of operation executable by said processor. A computer-readable script may be a computer program or control logic of a computer program product of an embodiment of the present invention.

It is not critical to the invention that the computer program be written in any particular computer language or to operate on any particular type of computer system or operating system. The computer program may be written, for example, in C++, Java, Perl, Python, Ruby, Pascal, or Basic programming language. It is understood that one may create such a program in one of many different programming languages. In one aspect of this invention, this program is written to operate on a computer utilizing a Linux operating system. In another aspect of this invention, the program is written to operate on a computer utilizing a MS Windows or MacOS operating system.

It would be understood by one of skill in the art that codes may be performed in any order, or simultaneously, in accordance with the present invention so long as the order follows a logical flow.

In one embodiment, the computer program has an input space for the user to insert the desired amino acid sequence and an output space where the generated nucleotide sequence is displayed. In one embodiment, the computer program has an editing mode, where the probability for selecting each NLS for each NLR may be modified as desired by the user.

Nucleotide Sequences for Optimization

A synthetic (or "optimized") nucleotide sequence may be generated for any nucleotide sequence encoding a polypeptide of interest, including but not limited to, sequences encoding pesticidal proteins, herbicide resistance proteins, fungal resistance proteins, hydrolytic enzymes, including enzymes altering the amount and/or nature of carbohydrate, protein, or lipid/oil in a plant grain, quality traits, or any other protein of interest. Pesticidal proteins include delta-endotoxin proteins, such as those from *Bacillus thuringiensis*.

By "pesticidal" is intended the ability to bring about death to at least one pest, or to noticeably reduce pest growth, feeding, or normal physiological development. An "insecticidal" compound is one that has this activity against a pest in the insect order. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein.

The following examples are offered by way of illustration and not by way of limitation.

EXPERIMENTAL

Example 1

Optimization of a Bacterial Delta Endotoxin Gene for Expression in *Zea mays* Using an Order 5 Statistical Model Step 1: Identification and collection of *Z. mays* cDNA sequences (Module A). Sequences of coding regions known in the art to be expressed in *Zea mays* were collected from public resources (e.g. GENBANK®). These sequences consisted of mRNAs, cDNAs, or genomic fragments representing coding sequences. As needed, the sequences were edited to remove non-coding regions (by preferentially identifying open reading frame (ORF) regions within the sequence population).

Step 2: Generation of an NLS stats Table for the *Zea mays* cDNA sequences using an N of 5. Sequences from *Z. mays* were analyzed using a 5-base sliding sequence window as described in module B. A table consisting of all possible 5-base sequences was generated, and counts recorded for each 5-base sequence observed in the *Z. mays* sequence set from Step 1. Observed counts were divided by the total number of observed 5-base sequences to generate raw frequency values. Observed raw frequency values were divided by expected frequency values to generate observed:expected ratios for all 5-base sequences (NLSs) in the *Z. mays* sequence set. Expected frequencies in this example were defined using a flat distribution model (that is, each NLS (5-base sequence) was considered equally likely within the 1,024 possible NLSs (5-base DNA sequences)). The resulting table is referred to as the NLS Stats Table. Observed:expected ratios were considered to approximate the probability of occurrence for each of the 5-base sequences observed.

Step 3. Replacement of low-probability 5-base sequences (NLSs) within the bacterial delta endotoxin gene with high-probability sequences. A candidate delta endotoxin gene (Axmi004; disclosed in U.S. patent application Ser. No. 10/739,610 filed Mar. 18, 2003) was examined by sliding window analysis to determine the relative likelihood of each 5-base sequence (NLS where N=5) within the gene. All gene sequence nucleotide positions were ranked in ascending order according to their probability of occurrence in *Z. mays*, in this case approximated by using the NLS Stats Table from Step 2. Beginning with the lowest-probability sequence positions, a set of silent substitutions was generated by identifying all possible NLSs (5-base substitutions) at that position that did not disrupt the gene reading frame or introduce mutations in the gene amino acid sequence (SNLSs). At each position, the 5-base silent substitution (SNLS) having the highest *Z. mays* observed:expected ratio (highest ranking in the NLS Stats Table) was substituted for the existing 5-base sequence. This cycle was repeated as described in module C, above, and iterated for several rounds until no additional silent changes that increased the net likelihood of the gene sequence were possible. The resulting sequence was considered the preliminary optimized gene.

Step 4. Removal of spurious ORFs from the preliminary optimized gene. ORFs not encoding the gene of interest were removed from the preliminary optimized gene by replacing NLSs in the preliminary optimized gene (5-base sequences) with SNLSs (5-base sequences) as described in module D, above. Substitutions were selected that disrupted any identified spurious open reading frame while not interrupting the primary open reading frame (in this case, the Axmi004 protein). This cycle was iterated until no spurious open reading frames larger than 75 amino acids remained in the optimized gene producing an "ORF-scrubbed optimized gene."

Step 5. Removal of undesirable short DNA sequences from the ORF-scrubbed preliminary optimized gene. Short DNA sequences encoding undesirable features, including restriction enzyme recognition sequences, were removed from the preliminary optimized gene by replacing NLSs in the preliminary optimized gene with SNLSs (5-base sequences) as described in module E, above. Substitutions that introduced spurious ORFs were disallowed. This cycle was repeated until no undesirable sites remained, resulting in a fully-optimized gene.

Step 6. Generation of a variant fully-optimized gene having reduced GC content. A variant of the fully optimized gene was generated by substituting NLSs in the fully optimized gene with SNLSs (5-base sequences) as described in module F, above. Substitutions that introduced spurious open reading frames or undesirable short DNA sequences were disallowed. All possible silent substitutions were evaluated, and those that had the least impact on observed:expected ratio while still decreasing net GC content were identified. Substitutions were made in this fashion iteratively until the total GC content of the gene was driven below a target threshold of 50.0%. This sequence was considered the sub-50% GC optimized gene.

Example 2

The following algorithms provide an example of a functional set of algorithms for carrying out methods of the invention.

Example 3

Generation of an Optimized Gene Sequence Using the Nucleotide Sequence

The following example shows an abbreviated log file generated by use of the algorithms of Example 2 to create an optimized gene sequence. Many log entries have been deleted and replaced with "DATA NOT SHOWN," which simply indicates that similar steps were performed but not listed in this example. Sequences shown in this example are listed in Table 1.

Optimizing sequence axmi004_original . . .
   Beginning round 1 of optimization.
   Updating at position 1222, oligo is TGAGA, raw score is 0.032, delta score is 4.664.
   Updating at position 403, oligo is TGAGA, raw score is 0.032, delta score is 4.134.
(DATA NOT SHOWN)
   Updating at position 1138, oligo is ACTTC, raw score is 0.127, delta score is 0.134.
   Round 1 completed. Sequence score is 70.241
(DATA NOT SHOWN)
   Beginning round 6 of optimization.
   Updating at position 1561, oligo is TGAGG, raw score is 0.091, delta score is 0.058.
   Round 6 completed. Sequence score is 233.679
   Beginning round 7 of optimization.
   Round 7 completed. Sequence score is 233.679
   Optimization complete.

Attempting to scrub spurious ORFs . . .
  Round 1, current ORF count is 10
  Largest spurious ORF is 354 amino acids, from nucleotide 824 to 1886.
    Solution found: TGCTG at position 1439, delta is −0.204.
  (DATA NOT SHOWN)
  Round 31, current ORF count is 2
  Largest spurious ORF is 75 amino acids, from nucleotide 406 to 631.
    Solution found: TGAGA at position 580, delta is −0.037.
Attempting to scrub disallowed sites . . .
  Round 1, current site count is 11.
  Attempting to scrub first incidence of site HindII, sequence AAGCTT.
  No matches found for site AAGCTT
  (DATA NOT SHOWN)
  Attempting to scrub first incidence of site BbsIRC, sequence GTCTTC.
    Site found at positions 1152 to 1158.
      Solution found: GGTGT at position 1151, delta is −0.144
Final cleanup in progress . . .
  Performing cleanup scan . . .
  Change made at position 1340, oligo is CAAAG, delta is 0.636
  (DATA NOT SHOWN)
Optimized sequence: axmi004_original_opt_full
Initial score: −127.61 Optimized score: 219.30
Initial GC percent: 34.92 Optimized GC percent: 55.59
Attempting GC drivedown to 0.500 . . .
  Scanning sequence for possible changes . . .
  Updating at position 1284, oligo is GGATC, delta is −0.012, new GC percent is 55.54.
  Updating at position 1625, oligo is AAGAT, delta is −0.024, new GC percent is 55.48.
  (DATA NOT SHOWN)
  Updating at position 155, oligo is ATTTG, delta is −0.363, new GC percent is 49.97.
Final cleanup in progress . . .
  Performing cleanup scan . . .
  Change made at position 1571, oligo is TGGGC, delta is 0.387
  (DATA NOT SHOWN)
Optimized sequence: axmi004_original_opt 0.5
Initial score: −127.61 Optimized score: 202.61
Initial GC percent: 34.92 Optimized GC percent: 49.71

Example 4

Generation of an Optimized Gene Sequence Using a Preliminary Optimization Step Based on the Amino Acid Sequence The following example shows an abbreviated log file generated by use of the algorithms of Example 2 to create an optimized gene sequence by performing a preliminary optimization step using the translated amino acid sequence. Many log entries have been deleted and replaced with "DATA NOT SHOWN," which simply indicates that similar steps were performed but not listed in this example. Sequences shown in this example are listed in Table 1.
Generating initial optimum nucleotide sequence . . .
  Degenerating sequence MSELKGK at position 0
  Degenerating sequence FKKSTNR at position 7
  Degenerating sequence TCCLLKI at position 14
  (DATA NOT SHOWN)
  Degenerating sequence EFIPVE at position 623
Optimizing junctions and low spots . . .
  Beginning round 1 of optimization.
  Updating at position 1213, oligo is CCTTC, raw score is 0.227, delta score is 2.248.
  Updating at position 1048, oligo is ACCGC, raw score is 0.027, delta score is 2.066.
  Updating at position 1111, oligo is CCAAC, raw score is 0.188, delta score is 1.600.
  (DATA NOT SHOWN)
  Updating at position 1129, oligo is GGGAC, raw score is −0.030, delta score is 0.032.
  Round 1 completed. Sequence score is 235.396
  Beginning round 2 of optimization.
  Updating at position 1630, oligo is ACAGG, raw score is −0.049, delta score is 0.270.
  Updating at position 328, oligo is TCGAG, raw score is 0.126, delta score is 0.159.
  Updating at position 1054, oligo is TCACC, raw score is 0.137, delta score is 0.042.
  Round 2 completed. Sequence score is 235.867
  Beginning round 3 of optimization.
  Updating at position 1056, oligo is ACCTC, raw score is 0.196, delta score is 0.044.
  Round 3 completed. Sequence score is 235.911
  Beginning round 4 of optimization.
  Round 4 completed. Sequence score is 235.911
  Optimization complete.
Attempting to scrub spurious ORFs . . .
  Round 1, current ORF count is 11
  Largest spurious ORF is 354 amino acids, from nucleotide 824 to 1886.
    Solution found: TGCTG at position 1439, delta is −0.700.
  Round 2, current ORF count is 12
  Largest spurious ORF is 306 amino acids, from nucleotide 1653 to 735.
    Solution found: TCAAA at position 1167, delta is −0.742.
  (DATA NOT SHOWN)
  Round 25, current ORF count is 2
  Largest spurious ORF is 75 amino acids, from nucleotide 406 to 631.
    Solution found: TGAGA at position 580, delta is −0.037.
Attempting to scrub disallowed sites . . .
  Round 1, current site count is 11.
  Attempting to scrub first incidence of site HindII, sequence AAGCTT.
  No matches found for site AAGCTT
  (data not shown)
  Attempting to scrub first incidence of site BsmBI, sequence CGTCTC.
    Site found at positions 194 to 200.
      Solution found: TCAGC at position 196, delta is −0.439
  Round 2, current site count is 10.
  Attempting to scrub first incidence of site HindITI, sequence AAGCTT.
  No matches found for site AAGCTT
  (DATA NOT SHOWN)
  Attempting to scrub first incidence of site PstI, sequence CTGCAG.
    Site found at positions 1188 to 1194.
      Solution found: TCCAG at position 1189, delta is −0.344

(DATA NOT SHOWN)
Round 11, current site count is 1.
(DATA NOT SHOWN)
Attempting to scrub first incidence of site BbsI_RC, sequence GTCTTC.
   Site found at positions 243 to 249.
      Solution found: TCGTG at position 241, delta is −0.493
Final cleanup in progress . . .
   Performing cleanup scan . . .
   Change made at position 629, oligo is AATCA, delta is 0.567
(DATA NOT SHOWN)
Change made at position 1852, oligo is TTTAT, delta is 0.112
Performing cleanup scan . . .
Optimized sequence: axmi004_DNA
Optimized score: 222.40
Optimized GC percent: 57.02

TABLE 1

Sequences described in Examples 3 and 4.

| Sequence | SEQ ID NO: |
|---|---|
| TGAGA | 29 |
| ACTTC | 30 |
| TGAGG | 31 |
| TGCTG | 32 |
| AAGCTT | 33 |
| GTCTTC | 34 |
| GGTGT | 35 |
| CAAAG | 36 |
| GGATC | 37 |
| AAGAT | 38 |
| ATTTG | 39 |
| TGGGC | 40 |
| CCTTC | 41 |

TABLE 1-continued

Sequences described in Examples 3 and 4.

| Sequence | SEQ ID NO: |
|---|---|
| ACCGC | 42 |
| CCAAC | 43 |
| GGGAC | 44 |
| ACAGG | 45 |
| TCGAG | 46 |
| TCACC | 47 |
| ACCTC | 48 |
| TCAAA | 49 |
| CGTCTC | 50 |
| TCAGC | 51 |
| CTGCAG | 52 |
| TCCAG | 53 |
| TCGTG | 54 |
| AATCA | 55 |
| TTTAT | 56 |
| MSELKGK | 57 |
| FKKSTNR | 58 |
| TCCLLKI | 59 |
| EFIPVE | 60 |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of optimizing a nucleotide sequence for expression in a target organism comprising:
   a) providing a nucleotide sequence of interest;
   b) providing a target database of nucleotide sequences, wherein the database is specific to a genus of the target organism;
   c) compiling a list of all possible N-length nucleotide sequences (NLS) for a given length of N, wherein N is less than the length of the shortest nucleotide sequence in the database, and wherein N is constant for each NLS;
   d) obtaining an observed frequency value for each NLS by counting the number of times each NLS is represented in the database and dividing by the total number of NLSs observed in the database;
   e) calculating the probability score for each NLS identified in step (c) with respect to the database provided in step (b) to generate an NLS Statistics Table, wherein the probability score represents the observed frequency of each NLS relative to its expected frequency of occurrence within the target database;
   f) identifying for one or more N-length region(s) (NLRs) of the nucleotide sequence of interest a corresponding set of NLSs that does not alter the amino acid sequence encoded by the nucleotide sequence of interest, wherein an NLS that does not alter the amino acid sequence encoded by the nucleotide sequence of interest is considered a silent NLS (SNLS), and wherein the length of N in the NLR is equal to the length of N in the NLS; g) calculating a delta score for each SNLS, wherein the delta score represents the difference between the probability score of the NLR of the nucleotide sequence of interest and each corresponding SNLS;

h) substituting one or more NLRs in the nucleotide sequence of interest with the corresponding SNLS having the largest delta score to generate an optimized sequence; and i) chemically synthesizing a nucleic acid molecule consisting of the optimized nucleotide sequence for expression in the target organism.

2. The method of claim 1, wherein step (h) further comprises:

1) scanning the optimized sequence generated in step (h) to identify any spurious open reading frames (ORF);

2) substituting one or more NLRs in the optimized sequence with a corresponding SNLS that disrupts the spurious ORF; and, 3) optionally repeating steps (1) and (2) until all spurious ORFs are removed from the sequence.

3. The method of claim 2, wherein step (h) further comprises:

4) setting a target G:C content for the optimized sequence of step (2) or step (3);

5) substituting one or more NLRs in the optimized sequence generated in step (2) or step (3) with a corresponding SNLS that drives the G:C content closer to the target G:C content; and, 6) optionally repeating steps (4) and (5) until the target G:C content is reached.

4. The method of claim 2, wherein step (h) further comprises:

4) scanning the optimized sequence generated in step (2) or (3) to identify any undesired short DNA elements;

5) substituting one or more NLRs in the optimized sequence with a corresponding SNLS that removes the undesired short DNA element; and, 6) optionally repeating steps (4) and (5) until all undesired short DNA elements are removed from the sequence.

5. The method of claim 4, wherein step (h) further comprises:

7) setting a target G:C content for the optimized sequence of step (6);

8) substituting one or more NLRs in the optimized sequence with a corresponding SNLS that drives the G:C content closer to the target G:C content; and, 9) optionally repeating steps (7) and (8) until the target G:C content is reached.

6. The method of claim 1, wherein step (h) further comprises:

1) scanning the optimized sequence generated in step (h) to identify any undesired short DNA elements;

2) substituting one or more NLRs in the optimized sequence with a corresponding SNLS that removes the undesired short DNA element; and, 3) optionally repeating steps (1) and (2) until all undesired short DNA elements are removed from the sequence.

7. The method of claim 6, wherein step (h) further comprises:

4) setting a target G:C content for the optimized sequence of step (2) or step (3);

5) substituting one or more NLRs in the optimized sequence generated in step (2) or step (3) with a corresponding SNLS that drives the G:C content closer to the target G:C content; and, 6) optionally repeating steps (4) and (5) until the target G:C content is reached.

8. The method of claim 1, wherein step (h) further comprises:

1) setting a target G:C content for the optimized sequence of step (h);

2) substituting one or more NLRs in the optimized sequence with a corresponding SNLS that drives the G:C content closer to the target G:C content; and, 3) optionally repeating steps (1) and (2) until the target G:C content is reached.

9. The method of claim 1, wherein said target database is specific to an organism of interest.

10. The method of claim 1, wherein said N-length is between 4 and 10.

11. The method of claim 10, wherein said N-length is between 5 and 7.

* * * * *